(12) United States Patent
Balaguer et al.

(10) Patent No.: US 9,561,304 B2
(45) Date of Patent: Feb. 7, 2017

(54) COMBINATION OF BLOOD AND OF BIPHASIC CALCIUM PHOSPHATE CERAMIC PARTICLES

(75) Inventors: Thierry Balaguer, Colomars (FR); Nathalie Rochet, Nice (FR); Christophe Trojani, Falicon (FR); Florian Boukhechba, Nice (FR); Georges Carle, Nice (FR)

(73) Assignees: Centre National de la Recherche Scientifique, Paris (FR); Centre Hospitalier Universitaire De Nice, Nice (FR)

( * ) Notice: Subject to any disclaimer, the term of this patent is extended or adjusted under 35 U.S.C. 154(b) by 499 days.

(21) Appl. No.: 13/001,055

(22) PCT Filed: Jun. 22, 2009

(86) PCT No.: PCT/FR2009/000749
§ 371 (c)(1),
(2), (4) Date: Apr. 8, 2011

(87) PCT Pub. No.: WO2010/007230
PCT Pub. Date: Jan. 21, 2010

(65) Prior Publication Data
US 2011/0182950 A1 Jul. 28, 2011

(30) Foreign Application Priority Data
Jun. 23, 2008 (FR) ...................... 08 03492

(51) Int. Cl.
| | | |
|---|---|---|
| *A61K 9/16* | (2006.01) | |
| *A61K 35/14* | (2015.01) | |
| *A61K 35/28* | (2015.01) | |
| *A61P 19/00* | (2006.01) | |
| *A61P 19/08* | (2006.01) | |
| *B65D 85/84* | (2006.01) | |
| *C12N 5/077* | (2010.01) | |
| *C12N 5/078* | (2010.01) | |
| *A61L 27/12* | (2006.01) | |
| *A61L 24/00* | (2006.01) | |
| *A61L 27/36* | (2006.01) | |

(52) U.S. Cl.
CPC ............ *A61L 27/12* (2013.01); *A61L 24/0005* (2013.01); *A61L 24/0068* (2013.01); *A61L 27/365* (2013.01); *A61L 27/3608* (2013.01); *A61L 27/3616* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 7,357,941 B2 | 4/2008 | Dalal et al. | |
| 2002/0161449 A1 | 10/2002 | Muschler | |
| 2004/0029699 A1 | 2/2004 | Lemaitre et al. | |
| 2004/0068266 A1 * | 4/2004 | Delmotte ........... | A61B 17/8816 606/92 |
| 2005/0226939 A1 | 10/2005 | Ramalingam et al. | |
| 2008/0014279 A1 | 1/2008 | Talton et al. | |
| 2008/0147065 A1 * | 6/2008 | McKay et al. .................. | 606/60 |
| 2008/0316855 A1 | 12/2008 | Ferrante et al. | |

FOREIGN PATENT DOCUMENTS

| | | | | |
|---|---|---|---|---|
| GB | WO 2008104762 A2 * | 9/2008 | ............ | A61L 27/12 |
| WO | 01 81243 | 11/2001 | | |
| WO | 02 068010 | 9/2002 | | |
| WO | 2006 015275 | 2/2006 | | |
| WO | 2006 058153 | 6/2006 | | |
| WO | WO 2006058153 A1 * | 6/2006 | | |
| WO | WO 2008/104762 A2 | 9/2008 | | |

OTHER PUBLICATIONS

Mankani, Biotechnology and Bioengineering, 72, 1, 2001.*
Arinzeh, Biomaterials, 26, 2005.*
Trojani, Biomaterials, 27, 2006.*
Hing, K. A. et al., "Microporosity Enhances Bioactivity of Synthetic Bone Graft Substitutes", Journal of Materials Science: Materials in Medicine, vol. 16, No. 5, pp. 467-475, XP019212185, ISSN: 1573-4838 (May 1, 2005).
International Search Report issued Oct. 15, 2009 in PCT/FR09/000749 filed Jun. 22, 2009.
U.S. Appl. No. 13/000,653, filed Dec. 22, 2010, Balaguer, et al.
Bouler et al., *Macroporous Biphasic Calcium Phosphate Ceramics: Influence of Five Synthesis Parameters on Compressive Strength*, J Biomed Mater Res, 1996, 32, 603-609.
Bouler et al., *Biphasic Calcium Phosphates: influence of Three Synthesis Parameters on the HA/β-TCP Radio*, J Biomed Mater Res, 2000, 51, 680-684.
Chevrier, A. et al., *Chitosan-Glycerol Phosphate/Blood Implants Increase Cell Recruitment, Transient Vascularization and Subchondral Bone Remodeling in Drilled Cartilage Defects*, Osteoarthritis and Cartilage 15 (2007) 316-327.
Fellah, B. H. et al., *Inflammatory Reaction in Rates Muscle After Implantation of Biphasic Calcium Phosphate Micro Particles*, J. Mater Sci.: Mater. Med. 18 (2007) 287-294.
Hertz, A et al., *Inorganic Materials for Bone Repair or Replacement Applications*, Nanomedicine, Future Medicine Ltd., vol. 2, No. 6 (2007) 899-918.
Malard, O. et al., *Influence of Biphasic Calcium Phosphate Granulometry on Bone Ingrowth, Ceramic Resorption, and Inflammatory Reactions: Preliminary in vitro and in vivo Study*, J. Biomed. Materl. Res. 46(1) (1999) 103-111.

(Continued)

*Primary Examiner* — Susan Tran
*Assistant Examiner* — William Craigo
(74) *Attorney, Agent, or Firm* — Alston & Bird LLP

(57) ABSTRACT

The invention relates to a biomaterial containing coagulated blood or coagulated bone marrow aspirate and biphasic calcium phosphate ceramic particles, to a production method thereof and to the use of same for the production of an implant that enables bone tissue regeneration.

25 Claims, 10 Drawing Sheets

(56) References Cited

OTHER PUBLICATIONS

Figure 1:
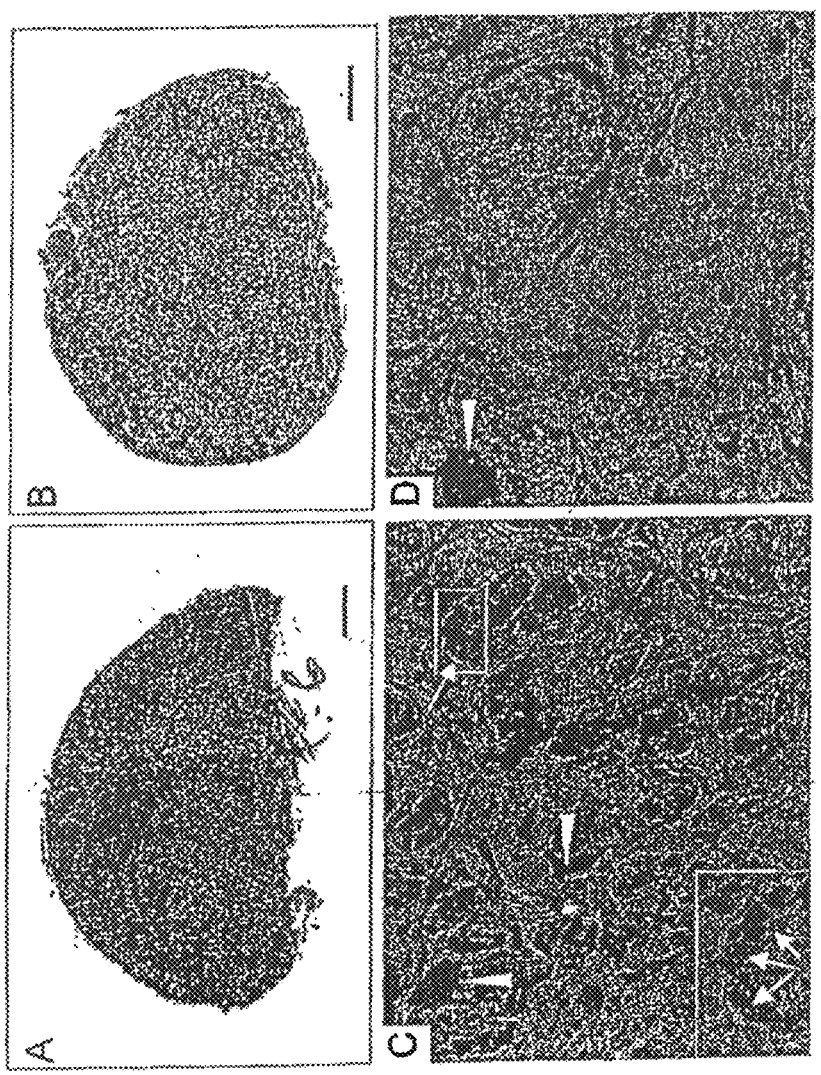

Nery et al., *Tissue Response to Biphasic Calcium Phosphate Ceramic With Different Ratios of HA/βTCP In Periodontal Osseous Defects*, J. Periodontol. Sep. 1992; 63(9): 729-35

Obadia et al., *Calcium-Deficient Apatite Synthesized by Ammonia Hydrolysis of Dicalcium Phosphate Dihydrate: Influence of Temperature, Time, and Pressure*, J Biomed Mater Res, 2006, 80(B), 32-42.

Okazaki, L. et al., *Blood-Filled Spaces With and Without Deproteinized Bone Grafts in Guided Bone Regeneration*, Clin. Oral Impl. Res., 16, 2005, 236-243.

Schmid, J. et al., *Blood-Filled Spaces With and Without Filler Materials in Guided Bone Regeneration*, Clin Oral Impl Res 8 (1997) 75-81.

Trojani, C. et al., *Ectopic Bone Formation Using an Injectable Biphasic Calcium Phosphate/Si-HPMC Hydrogel Composite Loaded With Undifferentiated Bone Marrow Stromal Cells*, Biomaterials 27 (2006) 3256-3264.

Wallkamm, B. et al., *Effect of Bioresorbable Fibres (Polyfibre®) and a Bioresorbable Foam (Polyfoam®) on New Bone Formation, A Short Term Experimental Study on the Rabbit Skull*, Clin. Oral Imp. Res. 14 (2003) 734-742.

Yildirim, M. et al., *Maxillary Sinus Augmentation Using Xenogenic Bone Substitute Material Bio-Oss® in Combination With Venous Blood*, Clin. Oral Impl. Res. 11 (2000) 217-229.

International Search Report for Application No. PCT/FR09/000748 dated Oct. 16, 2009.

Mankani, M. H., et al.; "*In Vivo Bone Formation by Human Bone Marrow Stromal Cells: Effect of Carrier Particle Size and Shape*;" Biotechnology and Bioengineering, vol. 72, No. 1; dated Jan. 5, 2001; pp. 96-107.

\* cited by examiner

COMBINATION OF BLOOD AND OF BIPHASIC CALCIUM PHOSPHATE CERAMIC PARTICLES

The subject of the invention is a novel biomaterial containing coagulated blood or coagulated bone marrow aspirate, and biphasic calcium phosphate ceramic particles, and a method for its preparation and its use for the manufacture of an implant allowing bone tissue regeneration.

The reconstruction of loss of bone substance, mainly of trauma and more rarely tumor origin, is one of the great difficulties encountered by orthopedic surgeons. Small size defects, from "narrow" pseudarthrosis (defect of consolidation of a fracture where the loss of substance is virtual) to bone loss of 5-6 cm, are most often the subject of an autologous transplant of spongy or corticospongy bone tissue removed from the iliac crest (gold standard). Large size defects ($\geq 6$ cm) require much more cumbersome procedures, vascularized bone transfers or Masquelet technique. Nevertheless, the quantity of available autologous bone is limited, bone consolidation remains uncertain and these various techniques mainly result in post-operative complications at the site of removal of the transplant.

Various biomaterials available in clinical practice make it possible to avoid, in theory, the disadvantages of autologous transplantation. Unfortunately, none of them rivals the results of bone transplantation and they never allow the reconstruction of loss of large size substance.

The majority of the bone substitutes currently studied combine biomaterials with mesenchymal stem cells obtained from bone marrow after several weeks of selection and cell culture in vitro. This approach is cumbersome and expensive, which limits the clinical benefits.

L. Okazaki et al., Clin. Oral Impl. Res., 16, 2005, 236-243 describe implants containing either demineralized bone powder or coagulated blood. Several authors have studied the combination of blood with synthetic biomaterials: J. Schmid et al., Clin. Oral Impl. Res. 1997:8:75-8 describe implants containing demineralized bovine bone powder and blood. A. Chevrier et al., Osteoarthritis and Cartilage (2007), 15, 316-327, describe implants containing a solution of polymer containing chitosan in a glycerol phosphate buffer and blood which coagulates in situ. B. Wallkamm et al., Clin. Oral Imp. Res., 14, 2003, 734-742 describe implants containing blood and a polylactic acid derivative (Polyfibre® or Polyfoam®). Yildérim M. et al., Clin. Oral Impl. Res., 2000, 11, 217-219 describe implants containing bovine apatite and venous blood. The document US 2008/0014279 describes a biomaterial consisting of a granular material coated with a polymer gel, and which may be mixed with any sort of liquid, in particular blood, in order to form a paste which is applied using a spatula or a syringe to the site where the bone defect has to be filled in. The document WO 02/068010 describes a composite material containing bone marrow, this material comprising a biocompatible and porous implantable matrix and a coagulated material, such as a coagulate of bone marrow, blood, plasma.

However, none of these implantable materials described in the prior art is free of disadvantages:

Materials requiring the culture of bone marrow cells before combining with a support (demineralized bone, synthetic polymer or the like) take a long time to use and require collecting bone marrow from the individual to be treated several weeks before fitting the implant, which multiplies the procedures and the risks associated therewith.

Biomaterials combining a support and noncoagulated blood do not allow an implant to be constructed.

While the combination of some support materials with coagulated blood has been proposed, the results obtained are not always satisfactory, in particular because the method does not allow the production of a homogeneous biomaterial.

Such materials resulting from the combination of a support and coagulated or noncoagulated blood have up until now been used in maxillofacial surgery where the problems of bone consolidation are less critical, but they have hardly or not at all been used in the repair of diaphyseal bones.

In the case of WO 02/068010, the method taught consists in using a support material consisting of porous demineralized bone in the form of granules having a minimum size of at least 1 mm, combined with demineralized cortical bone fibers of at least 5 mm, and with a coagulated material, preferably derived from bone marrow. All the examples proposed comprise bone marrow cells.

The invention makes it possible to overcome the disadvantages of the prior art, and in particular, it makes it possible to obtain an implantable biomaterial from a synthetic support, which is therefore easy to produce with constant and homogeneous properties, and coagulated blood, without the need to use culture steps, this material having excellent biocompatibility, allowing rapid reconstruction of bone tissue. The invention also allows the production of a bone of excellent quality in terms of hardness and vascularization. In addition, the method for manufacturing this biomaterial is simple, easy to carry out, does not require multiple procedures on the individual to be treated, is inexpensive compared to the prior art methods.

The biomaterial of the invention is in the form of a paste which comprises at least a biphasic calcium phosphate in the form of granules, substantially homogeneously mixed with coagulated blood.

The biphasic calcium phosphate, BCP, is used in numerous medical and dental applications. Biphasic calcium phosphate was first described as a bone repair material by Nery E B et al., J. Periodontol. 1992 September, 63(9): 729-35. BCP consists of a mixture of hydroxyapatite (HA) $Ca_{10}(PO_4)_6(OH)_2$ and beta-tricalcium phosphate $(Ca_3(PO_4)_2)$ (β-TCP). Its bioactivity and its bioresorbability may be controlled by the proportion of its constituent hydroxyapatite and β-TCP.

Biomaterials containing BCP have the advantage, compared to other synthetic biomaterials, of promoting osteogenesis.

BCP has been the subject of numerous studies: Fellah B. H. et al., J. Mater. Sci.: Mater. Med. (2007), 18, 287-294, have shown that the choice of a particle size of less than 20 μm promotes the inflammatory response of tissues, which could explain the fact that this particle size is particularly favorable to osteogenesis, as observed by Malard O. et al., J. Biomed. Mater. Res., 46(1), 1999, 103.

Mankani M. H. et al., Biotechnology and Bioengineering, 72(1), 2001, 96-107, have by contrast shown that calibrated BCP particles having a size ranging from 100 to 250 μm were those which caused the most bone reconstruction when they are combined with cultured bone marrow cells, while no bone formation was observed below 44 μm, and that good results are obtained with particles of up to 2 mm in size.

Trojani C. et al., Biomaterials, 27, 2006, 3256-3264, have shown that good osteoinduction could be obtained by the implantation of a BCP/hydrogel of Si-hydroxypropylmethyl cellulose composite material to which cultured bone marrow cells have been added, with calibrated BCP particles of 40 to 80 μm.

The latter two methods nevertheless require a step of collecting bone marrow cells and their culture.

The present invention is based on the following facts:
the observation by the inventors that BCP was endowed with anticoagulant properties,
the observation by the same inventors that a BCP with a chosen particle size combined with coagulated blood, or with a coagulated bone marrow aspirate, makes it possible to obtain very good osteogenesis and leads to a bone tissue of very satisfactory quality, with the aid of a method of great simplicity compared with those of the prior art.

The first subject of the invention is therefore the combination of a particular BCP defined below with coagulated blood or with a coagulated bone marrow aspirate. Advantageously, this combination is in the form of a malleable homogeneous paste.

This paste may be manipulated in order to adapt it to the size and shape of the defect to be filled in, while being careful not to apply excessive pressure to it which would damage or destroy its three-dimensional structure.

The BCP used in the present invention has a particle size of between 40 and 500 µm, preferably between 40 and 400 µm, more preferably still between 40 and 300 µm, and advantageously between 80 and 200 µm.

The BCP used in the invention consists of a high-temperature sinter that is ground and calibrated, for example by sieving, as granules having a chosen diameter. Advantageously, the BCP used in the invention comprises hydroxyapatite and β-tricalcium phosphate in an HA/β-TCP weight/weight ratio of between 5/95 and 95/5, preferably between 30/70 and 80/20, advantageously between 40/60 and 60/40.

Advantageously, this is porous BCP, with pore sizes ranging from 50 nm to 150 µm, preferably from 1 µm to 50 µm.

The granules or powder of tricalcium phosphate and hydroxyapatite may be obtained in accordance with the methods described by Bouler et al., J Biomed Mater Res, 1996, 32, 603-609; Bouler et al., J Biomed Mater Res, 2000, 51, 680-684; Obadia et al., J Biomed Mater Res, 2006, 80(B), 32-42. They are commercially available from the company GRAFTYS SARL.

If the prior art methods are applied to the BCP granulate, that is to say if BCP is mixed with a blood sample for example, blood coagulate is not obtained because BCP is endowed with anticoagulant properties. According to the method of the invention, BCP is mixed with a blood sample collected beforehand over an anticoagulant or collected without anticoagulant and brought immediately into contact with BCP in a donor compatible with the recipient of the biomaterial, and then at least one coagulating agent is added to the mixture with stirring. Preferably, the coagulating agent is a calcium derivative. Advantageously, the calcium-based coagulating agent is chosen from biocompatible calcium salts such as $CaCl_2$, $Ca(NO_3)_2$, $Ca(AcOEt)_2$, $CaSO_4$.

Among the other coagulating agents which can be used for carrying out the invention, thrombin may be mentioned. The mixing of BCP, blood, or marrow aspirate, and coagulating agent is continued during the entire coagulating step and is of an intensity suitable for allowing the formation of a homogeneous mixture of granules or particles of BCP and coagulated blood, or of coagulated marrow, and in particular the maintaining of BCP particles in suspension. If this stirring is excessive or not sufficiently vigorous, it does not allow the production of a homogeneous mixture. A person skilled in the art can visually control the formation of a homogeneous mixture.

In addition to BCP, the composition of the biomaterial may comprise optional additives such as: polymers, ceramic particles, pharmaceutical molecules, the conditions for using these materials being: their biocompatibility, the absence of a negative effect on the biomaterial setting reaction. Such additives which are well known to a person skilled in the art are intended to modify the rheology of the biomaterial, its behavior in vivo (hardness, resorption, osteogenesis) or to act on the appearance of infections or inflammatory phenomena (antibiotics, anti-infectives, anti-inflammatory agents).

It may also be possible to envisage introducing into the biomaterial of the invention active ingredients, such as therapeutic molecules, such as molecules intended to prevent or treat a pathology chosen for example from: a cancer, osteoporosis.

It is also possible to introduce natural or synthetic growth factors into the biomaterial of the invention. It is also possible to envisage the presence of biomarkers or contrast agents which promote the visualization, by medical imaging, of the resorption of the biomaterial and its fate in the body.

It is possible to envisage introducing into the biomaterial of the invention adipose tissue, or any other tissue or cell preparation, collected from the patient for whom the biomaterial is intended, this tissue or this preparation having been suspended beforehand in blood or in plasma or in physiological saline. Among the tissue or cell preparations, there may be mentioned adipose tissue, platelets, bone marrow cells.

It is also possible to envisage the presence of BCP with a different particle size, but preferably in a small quantity, advantageously <5% by weight/total weight of BCP because it has been observed that controlling the particle size allowed better formation of bone tissue (more rapid, better quality), and good resorption.

According to the method of the invention, the BCP is placed in a cavity of a closed and sterile container such as the inner cavity of a syringe. Blood or bone marrow aspirate, collected beforehand from a donor compatible with the recipient, is introduced into this container.

If the collected blood or bone marrow aspirate has to be stored for a period of more than a few seconds (5 to 10 seconds), it is immediately mixed after its collection with an anticoagulant in order to avoid its premature coagulation. The blood from the donor may for example be collected directly in a tube containing the appropriate quantity of anticoagulant agent.

The anticoagulant may be a chelator of calcium ions, such as for example sodium citrate, but also heparin for example.

The mixture of BCP and blood or bone marrow is prepared in the following preferred proportions:
from 10 to 90% by weight of BCP relative to the volume of blood (or of bone marrow), preferably from 50 to 90%, and more preferably still from 60 to 80%, in g/ml.

Advantageously, the blood is collected from the recipient themselves so as to ensure as much as possible the biocompatibility of the implant. According to one variant of the invention, the blood is replaced by a product derived from blood, such as plasma. Preferably, whole blood is used. In the entire application, including the claims, when the word blood is used, it includes in its definition blood-derived products such as plasma.

Preferably, in the implementation of the invention, blood or plasma is used whose collection does not require a surgical procedure.

According to one variant of the invention, the blood may be collected with the aid of a syringe in whose body the BCP and optionally additives have been placed beforehand.

After a first mixing of the BCP and the blood, the coagulating agent is also added to the mixture, for example by aspiration with the aid of the syringe if such a device is used.

The closed container containing the BCP, the blood and the coagulating agent is immediately stirred, so as to allow the formation of a homogeneous material. For example, if the mixture is prepared in a tube or in the body of a syringe, the container is placed in a rotary shaker whose speed is set according to the particle size of the BCP, such that the BCP particles remain in suspension while the coagulation occurs. According to one variant of the invention, the stirring may be produced by magnetic beads combined with a magnetic stirrer.

According to a preferred variant of the invention, the closed container containing the mixture of BCP, blood and coagulating agent is allowed to stand during the blood coagulation phase so as to allow the BCP to sediment and to form an implant saturated with BCP.

At the end of this step, the mixture is in the form of a homogeneous malleable paste containing a three-dimensional network of fibrin entrapping blood particles, plasma and other molecules that have been introduced into the composition.

According to the type of device that was used for the preparation of the biomaterial of the invention, the latter may then be applied with the aid of means which are most suited to the location where a bone defect has to be filled in:

With the aid of a tool such as a spatula without however disrupting the three-dimensional organization of the implant, or with the aid of the syringe or of another cylindrical device whose end would have been cut beforehand in order to form an opening suited to the rheology of the biomaterial of the invention.

Accordingly, another subject of the invention is a method for the manufacture of a biomaterial, this method comprising at least the following steps:
(i) mixing a BCP in the form of granules whose size is between 40 and 500 μm with blood, or with a bone marrow aspirate, in a proportion ranging from 10 to 90% by weight of BCP per volume of blood or marrow,
(ii) adding to the mixture of step (i) at least one coagulating agent in a sufficient quantity to cause the coagulation (of the blood or of the marrow),
(iii) mixing under conditions promoting the homogenization of the BCP while the coagulation occurs.

As has already been mentioned, in the method of the invention, steps (i) to (iii) may be carried out in the inner cavity of a syringe or in a tube closed at its ends. The coagulating agent may be chosen from calcium derivatives, such as those which were listed above, or from other coagulating agents such as thrombin for example.

The subject of the invention is also a method for filling in a bone defect, this method comprising the steps listed above and additionally comprising a step of applying the biomaterial obtained in step (iii) in the space where a bone defect has been observed. This method may additionally comprise tissue incision and suture steps.

Depending on the size and configuration of the bone defect, the filling in by the biomaterial of the invention may be associated with an osteosynthesis which makes it possible to confer on the affected tissue the mechanical strength required while the bone reconstruction is in progress at the site of implantation of the biomaterial of the invention.

As the inventors observed, the implantation of the biomaterial of the invention made it possible to induce the formation of bone tissue within a short period (a few weeks), this bone tissue being quite abundantly vascularized.

By contrast, it was observed that the implantation of a biomaterial obtained by the same method with a BCP having a particle size of less than 40 μm did not make it possible to obtain the formation of bone tissue of sufficient quality and within satisfactory periods. The implantation of a biomaterial obtained by the same method with a BCP having a particle size greater than 500 μm leads to an implant whose resorbability is lower.

Another subject of the invention consists of a kit for carrying out the method of the invention, this kit comprising the combination of a BCP having a particle size of between 40 and 500 μm, preferably between 40 and 400 μm, advantageously between 40 and 300 μm and more preferably still of 80 to 200 μm, with at least one coagulating agent. Preferably, the coagulating agent is derived from calcium. Advantageously, the coagulating agent is $CaCl_2$.

The quantity of coagulating agent is calculated in order to compensate for the anticoagulant effect of BCP and optionally of the anticoagulant agent which is combined with the blood collected.

The concentration of coagulating agent in the mixture of blood and BCP should be preferably between 1 and 50 mM, more preferably still between 3 and 35 mM, in particular in the case where the coagulating agent is based on calcium. The coagulating agent should be preferably added as an aqueous solution so as not to exceed 2 volumes of solution of coagulating agent by weight of BCP in ml/g.

The concentration of the solution of coagulating agent may vary so as to respect these two constraints, and when using preferably a solution of coagulating agent having a concentration of less than 120 mM, in particular when the coagulating agent is a calcium salt.

If the blood is collected over anticoagulant, the effect of the anticoagulant agent and the effect of the biomaterial should be compensated for.

For example, for blood collected over sodium citrate under conventional conditions (of the trademark Vacuette®, available from the company Greiner Bio-One, or of the trademark Vacutainer®, available from the company Becton Dickinson) and in the proportions of 50 mg of BCP and 100 μl of blood, we add $\frac{1}{5}^{th}$ of the final volume (that is 20 μl) of a calcium solution at 80 mM (final concentration 13.3 mM). The concentration of the solution may be up to 120 mM. Above, there may be an excess of calcium, which again inhibits the coagulation.

If the blood is not collected over an anticoagulant, the blood is collected directly over the biomaterial and the calcium is added in a second instance. In this case, it is possible to add $\frac{1}{5}^{th}$ of the blood volume of an aqueous solution of calcium salt having a concentration ranging from 12 mM to 60 mM approximately.

Such a combination may be in the form of a sterile kit comprising:
(a) a device comprising a sterile inner cavity in which the BCP is placed,
(b) a sterile reservoir containing the coagulating agent.

The reservoir (b) may be part of the device (a) or may be a separate entity such as a tube or a bottle from which the coagulating agent may be removed and transferred to the inner cavity of the device (a), or a syringe allowing the injection of the coagulating agent into the cavity where the BCP is placed.

Advantageously, the device (a) comprises means allowing the introduction of blood into the inner cavity: for example means allowing the collection of a blood sample either directly from an individual, or from a reservoir, or means allowing the injection of a blood sample into the inner cavity so as to allow mixing with the BCP. It is possible to envisage that the blood collected is directly introduced into the cavity comprising the BCP or that it is collected in the reservoir where the anticoagulant is placed and then the whole is transferred into the cavity where the BCP is present. In the case where a bone marrow aspirate is used, provision is made for a means for aspiration of the bone marrow.

The inner cavity of the device (a) has a size allowing the introduction therein of the quantity of blood or marrow necessary to produce the biomaterial of the invention, as well as the other constituents of the mixture such as: coagulating agent, active ingredients, tissue or cell preparations.

Also advantageously, the device (a) comprises means allowing the application of the biomaterial in the zone where a bone defect has been observed.

Such a device may consist of a cylindrical device such as a tube or a syringe as is illustrated in the experimental section.

It is also possible to envisage using a device such as the one described in WO 02/068010 comprising a tube in which the BCP is stored, into which the blood and the coagulating agent are injected and to which a piston may be fitted so as to release the biomaterial once it has been formed.

It is also possible to envisage using a device of the Vacutainer® type, that is to say tubes under vacuum to which a syringe is fitted which makes it possible to collect a predetermined quantity of blood, these tubes being pre-conditioned with BCP in their inner cavity.

Another subject of the invention consists of an implantable biomaterial comprising a BCP in the form of granules whose size has been defined above, dispersed substantially homogeneously in a three-dimensional network of blood proteins or in a network of bone marrow proteins.

Advantageously, this biomaterial comprises a BCP as defined above and a coagulate of blood (or marrow) proteins in the form of a substantially homogeneous mixture having the appearance of a malleable paste.

The expression malleable paste is understood to mean a material which itself does not flow, as would a liquid, but whose mechanical strength is sufficiently low to be able to be molded under the effect of pressure exerted manually by an individual, in particular with the aid of an instrument such as a spatula or the piston of a syringe.

Such a biomaterial may be used for the manufacture of a bone implant, whether this involves filling in a fracture, a loss of substance of trauma or tumor origin, a defect following a surgical procedure, or helping to fit a prosthesis.

The biomaterial may be introduced, as illustrated in the examples, by a surgical procedure in the zone where a bone defect needs to be filled in. After incision, the biomaterial is implanted and the incision is closed again.

The biomaterial of the invention may be combined with an osteosynthesis of greater mechanical strength, so as to allow the stability of the assembly while awaiting the colonization of the deficient zone by the bone tissues.

It is possible to envisage combining it with a prosthesis. Coating the prosthesis with the biomaterial of the invention makes it possible to promote the implantation of living bone tissue in or around the prosthesis.

The biomaterial of the invention may also be used in vitro or ex vivo as support for the production of bone tissue:

Indeed, the culture of bone cells around this biomaterial makes it possible to produce a bone tissue that can be subsequently implanted.

Another subject of the invention is the use in vitro or ex vivo of a biomaterial as described above for producing a bone implant.

It is possible, according to the invention, to culture bone cells on the biomaterial of the invention in a mold having the shape of the implant which it is desired to manufacture. The culture of cells under these conditions makes it possible to obtain a biocompatible implant having the appropriate shape and dimensions.

EXPERIMENTAL SECTION

Figures

Figure 2:
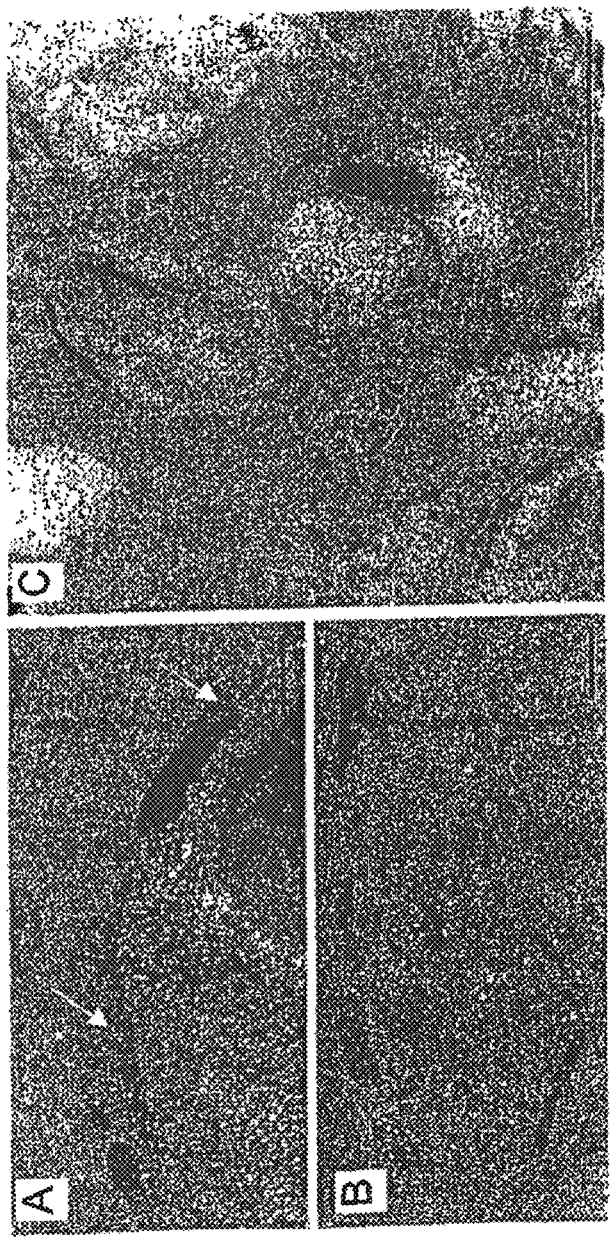

FIG. 1: Formation of bone tissue by an implant of coagulated blood around BCP particles.
Cross sections of implants stained with HES after 4 weeks of implantation at a subcutaneous (A and C) and intramuscular (B and D) site.
  Scale: A and B: 500 µm
  C and D: 50 µm
  White arrows: osteoblasts
  Black arrows: osteocytes
  Black arrowheads: blood vessels
  White arrowheads: osteoclasts FIG. 2: Section of blood/BCP implants after 4 weeks of implantation.
  (A): hybridization with immune serum showing the brown color of osteocalcin in the cytoplasm of cells (white arrow)
  (B): hybridization with nonimmune serum—scale: 10 µm
  (C): Goldner stain—scale: 50 µm
  Black arrows: vessels and osteocytes.

Figure 3:
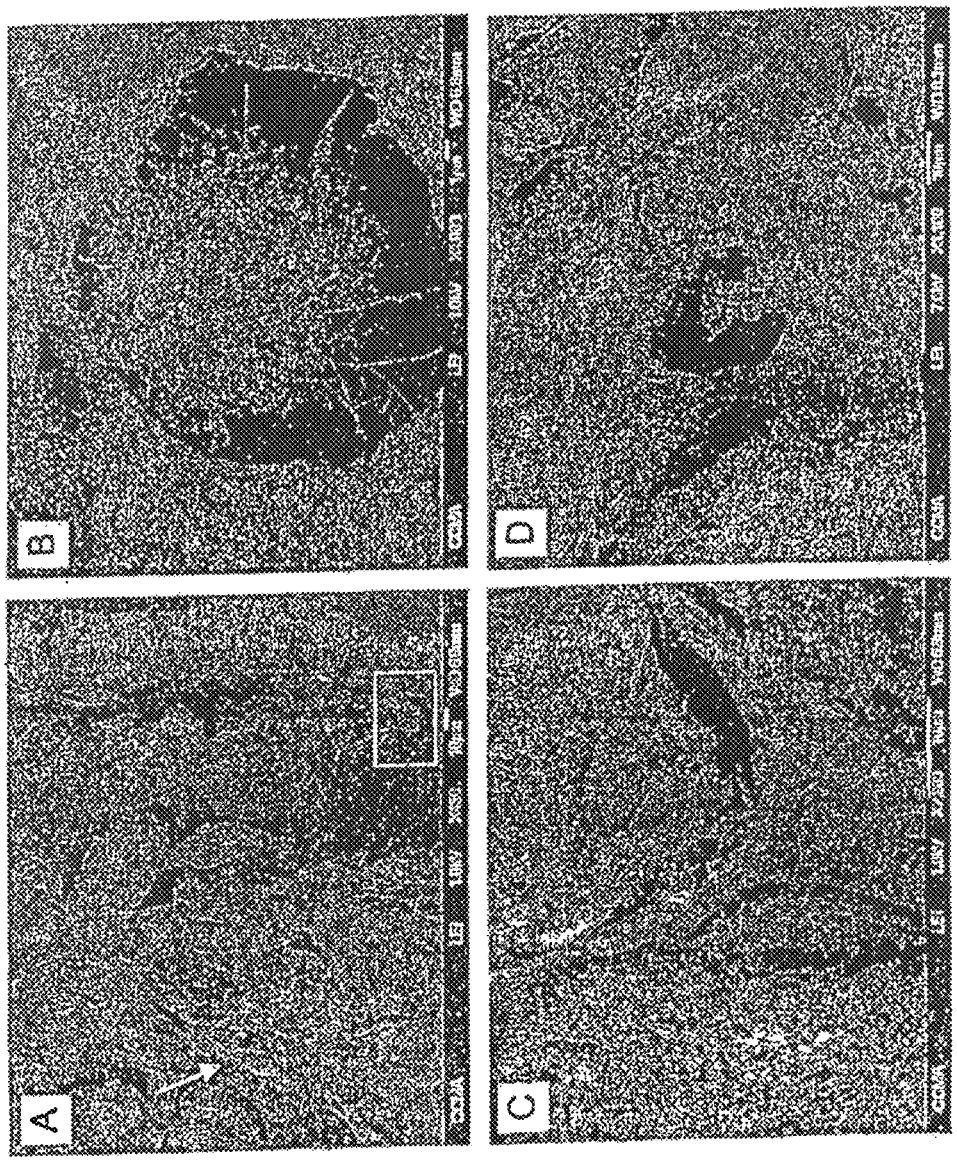
Figure 4:
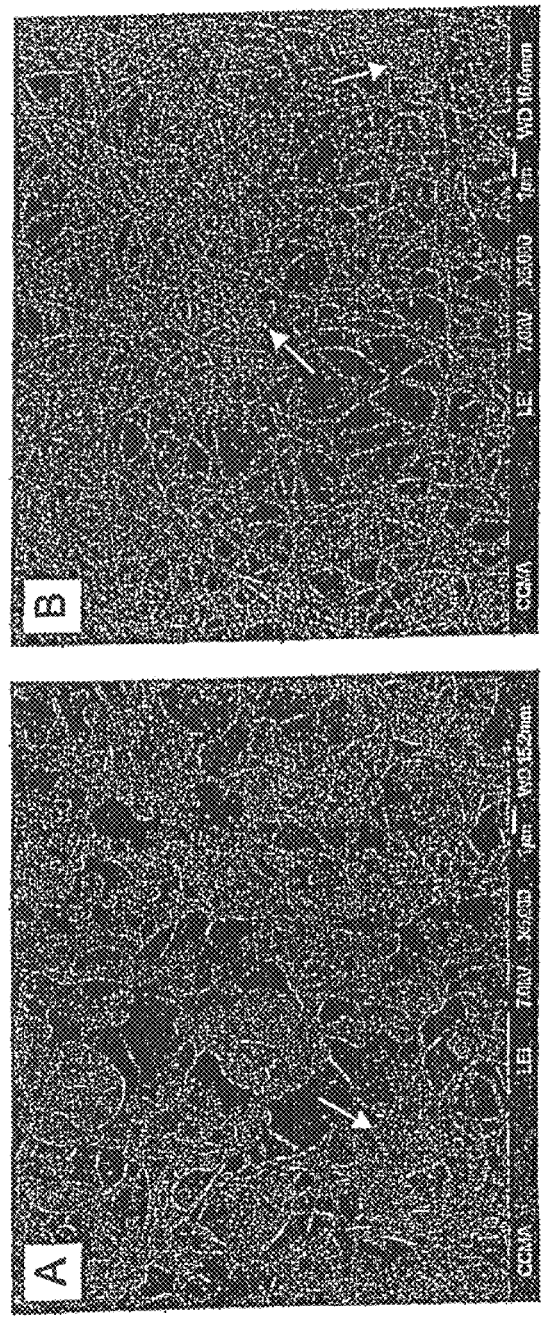
Figure 5:
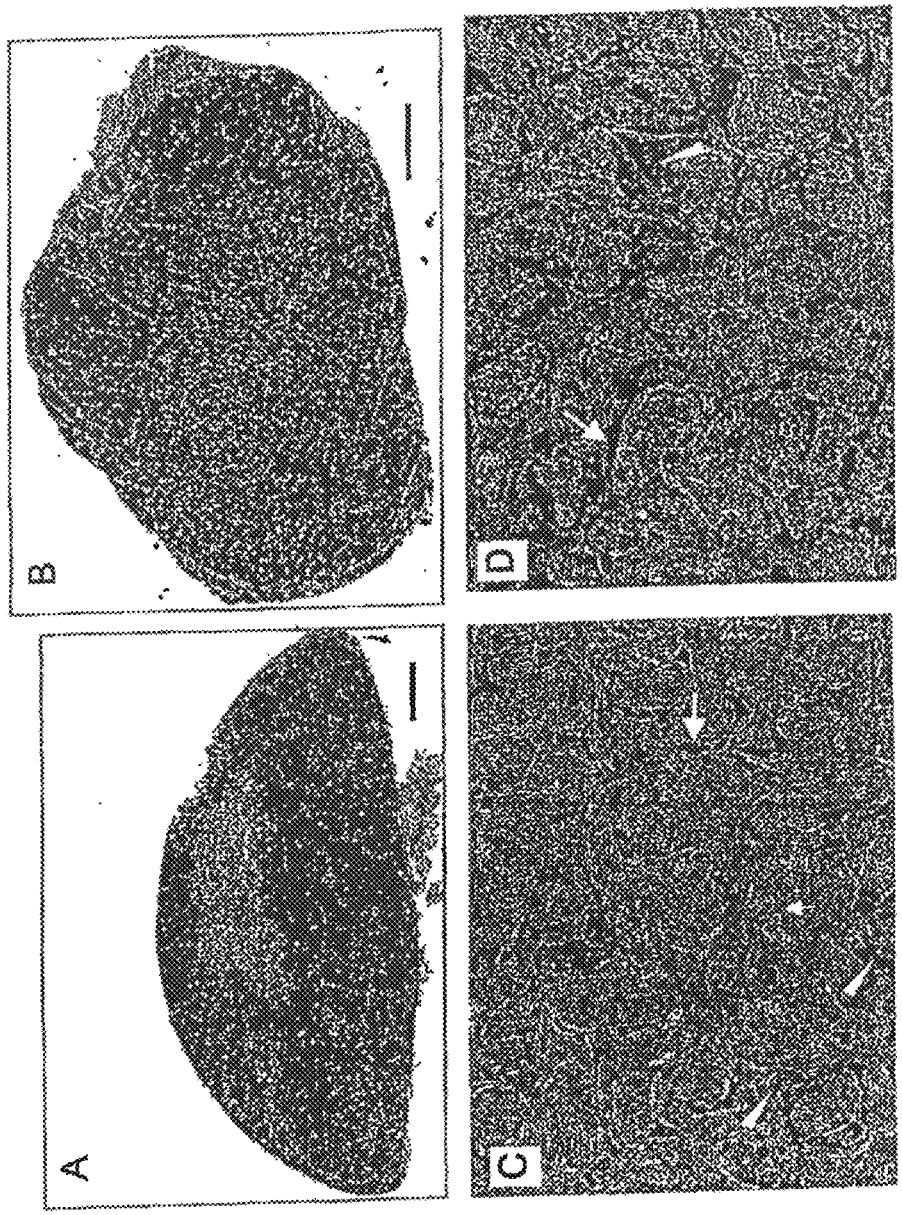

FIG. 3: Scanning electron microscopy of 4-week-old blood/BCP implants
  (A) collagen matrix in the intergranular space—scale: 10 µm
  (B) magnification of (A)—scale: 1 µm
  (C) two osteoclasts attached to the granules with 2 to 3 visible nuclei—scale: 10 µm
  (D) functional capillary—scale: 10 µm FIG. 4: Scanning electron microscopy of implants
  (A) BCP/coagulated blood
  (B) BCP/coagulated plasma
  Scale: 1 µm FIG. 5: Formation of bone tissue from BCP/plasma implants after 4 weeks of implantation
  Subcutaneous sites (A, C)
  Intramuscular sites (B, D)
  Scale: 500 µm (A, B)
    50 µm (C, D)

Figure 6:
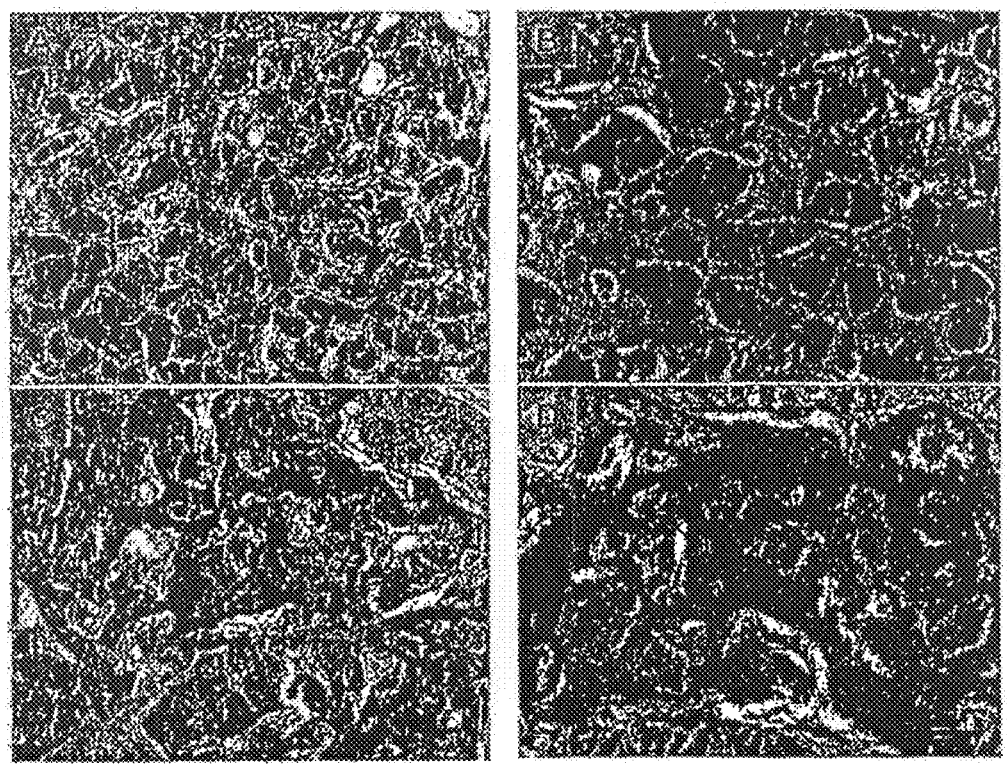

FIG. 6: Comparison of the osteogenic properties of the biomaterial prepared from blood of C57BL/6 mice (A, B) and human blood (C, D) combined with BCP microparticles (40-80 µm), after subcutaneous implantation in nude-type immunosuppressed mice. Observation at low (A, C) and high (B, D) magnification.
  Scales: 100 µm.

Figure 7:
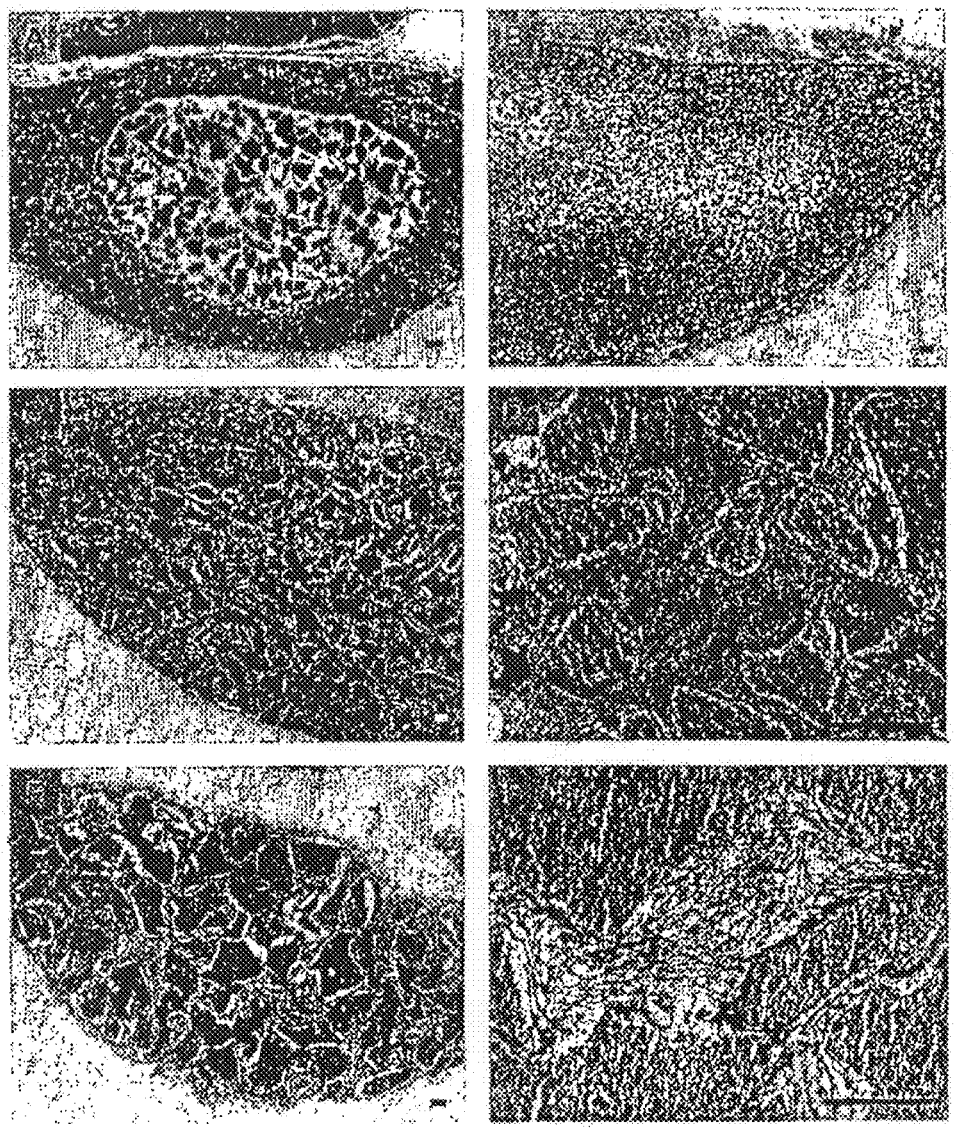

FIG. 7: Influence of the size of the BCP microparticles on bone formation after subcutaneous implantation in mice. Implants were prepared from the blood of C57BL/6 mice combined with BCP in the form (A) of a large quantity of fine dust having a size of less than 40 µm mixed with particles of 80-200 µm; (B) of particles of 40-80 µm; (C, D)

of particles of 80-200 µm; (E, F) of particles of 200-500 µm. Figures D and F correspond to views at higher magnification of the implants C and E respectively. Scales 100 µm.

Figure 8:
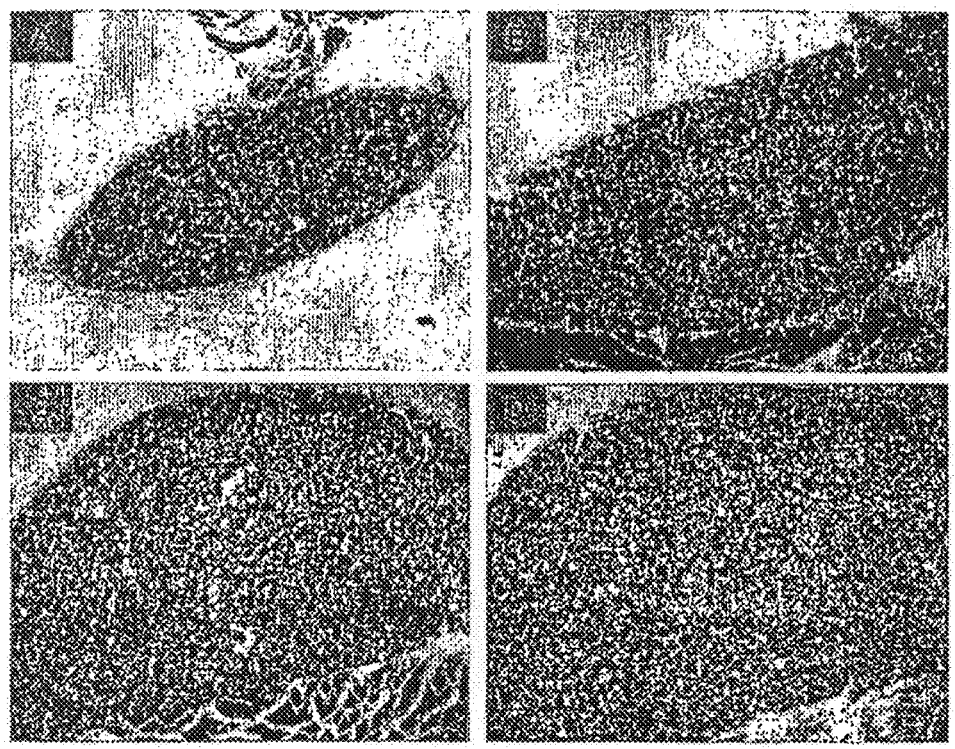

FIG. 8: Implants prepared from 100 µl of C57BL/6 mouse blood and increasing quantities of microparticles of BCP 40-80 µm: (A) 10 mg, (B) 30 mg, (C) 50 mg and (D) 70 mg. Scale: 100 µm.

Figure 9:
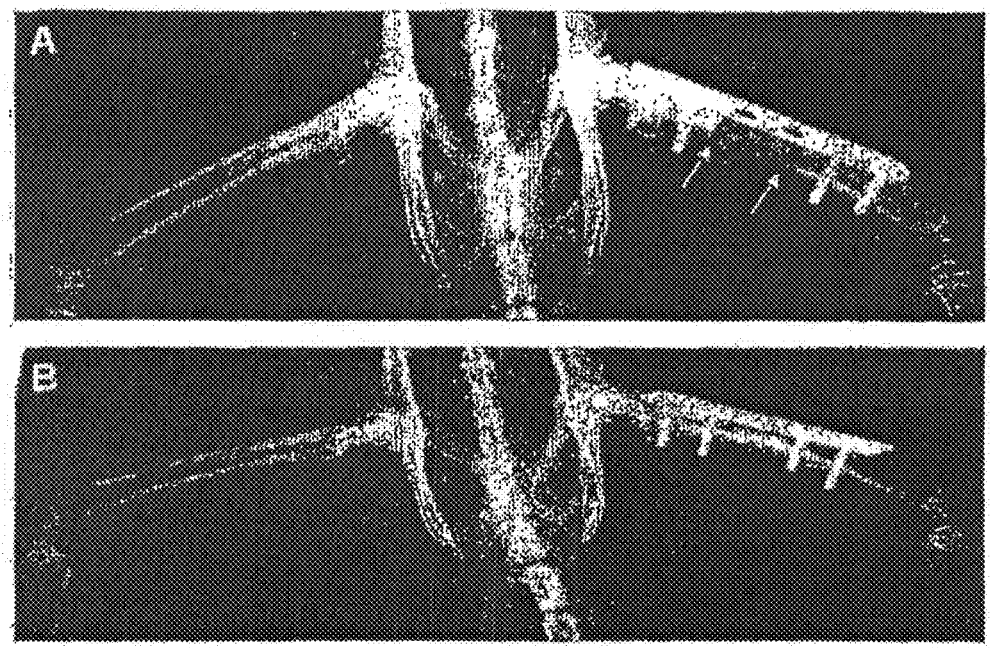

FIG. 9: X-rays in dogs—implants prepared from coagulated whole blood around calibrated BCP microparticles (80-200 µm): (A) BCP/blood with a ratio of 50%, the microparticles being maintained in suspension in the blood during the coagulation phase (method No. 1); (B) BCP at maximum concentration in the blood, the microparticles sedimenting during the coagulation (method No. 2). The white arrows indicate the presence of a radiotransparent line between the diaphyseal ends and the implant.

Figure 10:
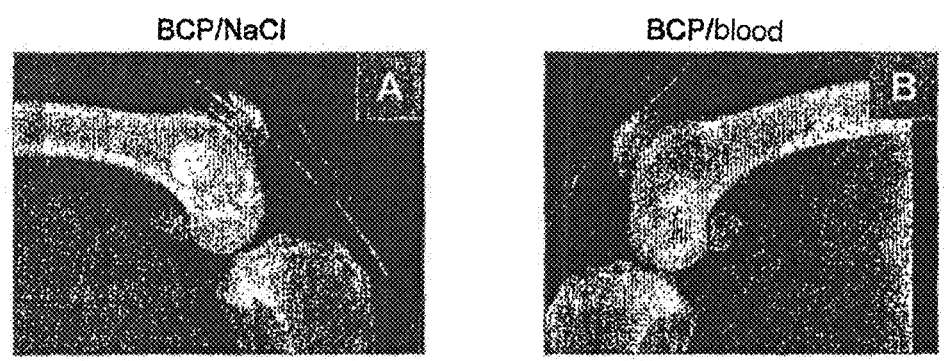

FIG. 10: Implantation in BEAGLE dogs. Post-operative x-rays. (A) to the left, the implant consists of BCP alone. (B) to the right, it consists of the BCP/blood mixture with a maximum ratio of BCP according to method 2 of preparation of the implants.

1. PRINCIPLE

This is an instant procedure, carried out in an operating room. It consists in mixing, in the body of a polypropylene syringe, BCP particles and autologous whole blood (50% w/v) collected over an anticoagulant that is a chelator of calcium ions. The addition of $CaCl_2$ makes it possible to initiate the coagulation. The syringe is then placed for 10 minutes at room temperature on a rotary mixer, which makes it possible to maintain the BCP particles in suspension in the blood during the course of the coagulation. A homogeneous distribution of the particles in the coagulated blood is thus obtained. The end of the syringe is then cut and the implant pushed out of the syringe with the aid of the piston and placed at the site of implantation.

Results Obtained in Animals (C57BL/6 Mice):

The implantation of the biomaterial at the ectopic site (subcutaneous and intramuscular) demonstrates its osteoinductive properties, with implants that are completely colonized by a mineralized immature bone tissue that is very richly vascularized after 4 weeks.

2. MATERIALS AND METHODS

2.1. Particles of Biphasic Calcium Phosphate

The biphasic calcium phosphate (BCP) biomaterial is composed of 60% hydroxyapatite (HA; $Ca_{10}(PO_4)_6(OH)_2$) and 40% tricalcium phosphate (TCP; $Ca_3(PO_4)_2$). The calibrated BCP particles between 80 and 200 microns were supplied by the company GRAFTYS SARL (Aix-en-Provence, France). The particles were sterilized by heating at 180° C. for two hours.

2.2. Preparation of the Implants and Surgical Procedure

—Subcutaneous Implantation in Mice

The experiments were performed in accordance with the regulations of the Direction of Veterinary Services (Direction des Services Vétérinaires) and authorized by the Regional Ethics Committee for Animal Experimentation (Comité Régional d'Ethique pour l'Expérimentation Animale (CREEA)). Whole blood is collected over sodium citrate (anticoagulation) by intracardiac puncture from anesthetized ten-week-old C57BL/6 mice. For some experiments, the plasma was prepared from whole blood by centrifugation at 1800 g for 15 minutes.

Method 1: The implants are prepared by mixing 100 µl of whole blood (or plasma) with 50 mg of BCP particles in a 1 ml syringe. The activation of coagulation is then obtained by adding 20 µl of a 1% $CaCl_2$ solution. During the period of coagulation (5 to 10 minutes), the syringe is placed on a roller of the New Brunswick tissue culture roller type, model TC-7 M1053-4005). This allows a rotational movement of the syringe on itself and maintenance of the BCP particles in suspension in the clot. After cutting the end of the syringe, the implants are pushed out of the syringe by means of the piston and implanted subcutaneously (SC) or intramuscularly (IM) in C57BL/6 mice.

Method 2: The implants are prepared with a maximum concentration of particles and therefore a maximum BCP/blood ratio. For that, the BCP/blood/calcium mixture is maintained in a fixed position for the duration of the coagulation so as to allow the microparticles to sediment naturally in the blood. It is thought that a maximum concentration of microparticles in the coagulated blood is thus obtained.

The subcutaneous implants were placed under the skin in a dorsal position and the intramuscular implants were placed in each thigh between the muscle masses after dissection. At each of the sites (SC and IM), it is checked that no bleeding was induced during the implantation.

In each implantation experiment, the C57BL/6 mice are anesthetized by inhalation of 4% isoflurane. Two SC implants and two IM implants are placed for each mouse. In some experiments, each mouse received a blood/BCP implant and a plasma/BCP implant at each site. After 4 to 8 weeks, the animals are sacrificed by inhalation of $CO_2$ and the implants removed for analysis.

—Implantation at a Bone Site in Rats

The protocol which we applied in rats was approved by the regional ethics committee for animal experimentation (NCA/2007/12-06). These preliminary experiments were carried out at the central animal house (Animalerie Centrale) of the Nice faculty of medicine.

We used a model of loss of femoral diaphyseal, interruptive, segmental, bone substance of critical size (6 mm) combined with plate-screw osteosynthesis, a model developed in our laboratory. We operate on a single femur per rat, the loss of substance is filled in with our biomaterial, autologous whole blood/BCP (80-200 µm). The rats are monitored clinically (absence of pain, deambulation, general condition) and radiologically by photographs at D0, D7, D15, D30, D45, D60 and D90. At the end of the third month, the animals are sacrificed, the femurs are collected and, after ablation of the osteosynthesis material, the bones are fixed in formalin before being embedded in methyl methacrylate resin and histological study.

During the first procedures, the implants were made to the size of the bone defect, with a proportion of particles of 50% weight/volume, that is 75 mg of BCP per 150 µl of whole blood collected from the animal pre-operatively. The coagulation is initiated by the addition of 15 µl of 2% $CaCl_2$ and the homogenization is produced by continuous rotation until coagulation is obtained so as to maintain the BCP particles in suspension in the blood and ensure the homogeneity of the biomaterial.

—Implantation at a Bone Site in BEAGLE Dogs

This is a model of loss of calibrated cylindrical cavitary bone substance of critical size in the region of the lateral femoral condyles, produced on adult dogs of the Beagle breed. For each dog, the 2 femoral condyles were tackled. Whole blood (3.5 ml) is collected at the beginning of the procedure, by puncture in the region of the jugular vein of the animal and is used to prepare the biomaterial. Cylindrical bone loss of 8×10 mm is produced in the region of each external femoral condyle and the bone sequestra are carefully removed by washing with physiological saline and aspiration.

Each animal received two implants of different composition but prepared so as to completely fill in the defect created, that is to say:

On the one hand, the biomaterial to be tested consists of a mixture of BCP (80-200 µm) and blood with a ratio of 50% weight/volume or 330 mg of BCP and 660 µl of whole blood. The BCP particles are maintained in suspension during the coagulation by rotation of the syringe which served to prepare the mixture.

On the other hand, BCP alone is implanted, moisturized in physiological saline, that is 660 mg, occupying the same volume as the controlateral implant.

The duration of the experiment is 8 weeks.

Post-operative x-rays were taken immediately and at the end of the experiment at the ENVN.

2.3. Histological Analysis

The dissected implants are fixed for 24 hours in a 10% buffered formalin solution. Each implant is then cut into three pieces which are decalcified or not in a 10% (w/v) ethylenediaminetetraacetic acid (EDTA) solution for 24 hours at room temperature and then embedded in paraffin. Sections of 4 µm are prepared, deparaffinized, moisturized and stained with hematoxylin, erythrosin, saffron (HES). The sections are then examined by optical microscopy using a Zeiss Axioskop microscope. The photos are taken with an AxioCam HRc color camera (Zeiss, Le Pecq, France). In order to quantify the surface areas occupied by the fibrillar bone, on the one hand, and by the BCP particles, on the other hand, each image of implant was subdivided into three zones having a surface area equal to 0.6 mm$^2$ along the median axis of the implant. In each of these three zones, the area occupied by the fibrillar bone tissue was measured using the AxioVision Rel. 4.6 software. This analysis was carried out for three SC implants and three IM implants. The number of vessels and osteoclasts was evaluated in these same zones by counting the capillaries and the multinucleated giant cells respectively under the light microscope (100×) by two different observers. The density of osteoclasts and vessels is expressed per mm$^2$ in the form of a mean±standard deviation. The statistical test used is the Student's T test. The significance was defined for a p value of less than 0.05.

2.4. Goldner Staining

Sections of nondecalcified implants having a thickness of 7 µm were stained by the Goldner's Trichrome method which makes it possible to evaluate the mineralization of bone tissue and to distinguish the mineralized tissue (in blue/green) from the nonmineralized osteoid tissue (in red). Briefly, the deparaffinized sections are rehydrated and then incubated in the presence of Weigert's hematoxylin for 20 min, rinsed with running water and differentiated in the presence of 1% acid alcohol, washed with running water for 5 min and then rinsed with distilled water. The sections are then stained by incubating in a solution of xylidine Ponceau/acid fuchsin/azophloxin/acetic acid for 5 min, rinsed in 1% acetic acid, incubated in the presence of phosphmolybdic acid/orange G for 20 min, rinsed in 1% acetic acid, stained in the presence of light green/acetic acid for 5 minutes, washed in 1% acetic acid for 5 minutes, dried and mounted in Entellan mounting medium (Merck, Darmstadt, Germany).

2.5 Immunohistochemistry of Murine Osteocalcine

We used an immunopurified polyclonal antibody to mouse osteocalcin, directed against a synthetic peptide corresponding to amino acids 1-20 of the N-terminal end of the protein (Alexis Biochemicals, Lausanne, Switzerland). Briefly, 7 µm sections in paraffin were deparaffinized, rehydrated in ethanol, washed in PBS and incubated for 30 minutes in the presence of 0.3% $H_2O_2$ in PBS. After two washes in PBS, the slides were incubated in the presence of 1.5% goat serum (blocking buffer) for 30 min. After washing in PBS, incubation in the presence of a biotin-labeled antibody to rabbit immunoglobulins and the procedure for visualization with peroxidase were performed using the ABC labeling kit (sc-2118, Santa Cruz, Calif., USA). The sections were then incubated in the presence of peroxidase substrate for 10 min and the cellular nuclei stained with hematoxylin for 3 min. After dehydration, the mounting is performed in Entellan mounting fluid (Merck). The controls are produced by incubating the slides in the presence of blocking buffer.

2.6. Scanning Electron Microscopy

The implants consisting of coagulated blood/BCP or coagulated plasma/BCP, before and after four weeks of implantation, were fixed for 12 hours at 4° C. in a buffered glutaraldehyde solution. The samples were then washed and incubated in the presence of 30% glycerol for 1 h and then frozen in liquid nitrogen and fractured. After dehydration in the presence of increasing concentrations of ethanol, they were immersed in hexamethyldisilazane (Sigma-Aldrich, L'isle d'Abeau Chesnes, France) for 5 min and then dried at room temperature. They were then fixed on aluminum supports and then coated with a layer of gold-palladium (Polaron E5100, UK). The examination was then performed using a scanning electron microscope of the JEOL 6700F type (Japan).

3. RESULTS

3.1. Macroscopic and Microscopic Analysis of the Subcutaneous and Intramuscular Implants of Coagulated Blood/BCP The implantation of coagulated blood in the absence of BCP particles did not allow the formation of bone tissue. After four weeks, only a small quantity of fibrous tissue was found at the site of implantation.

Dissection and macroscopic examination of the implants of coagulated blood around BCP particles after 4 and 8 weeks made it possible to observe their firm consistency and the presence of numerous small vessels at their surface. No inflammation of the host tissue was observed.

Histological analysis of the paraffin sections of blood/BCP implants after 4 weeks of implantation revealed a complete and reproducible colonization of the entire interparticle space by immature bone tissue in close contact with the BCP both for the SC (FIG. 1A) and IM (FIG. 1B) implants. Examination at higher magnification suggests that the collagen matrix is more mature at the IM site (FIG. 1D)

than at the SC site (FIG. 1C). To evaluate the quantity of fibrillar bone developed in the interparticle space, the ratio between the areas occupied by the bone tissue and the areas occupied by the BCP was calculated as described under Materials and Methods. This made it possible to show a significant difference between the SC and IM sites with 49.63±5.08% of bone tissue in the IM implants and 42±8.33% in the SC implants (n=9, p=0.035). All these results show that the interparticle space is completely colonized in both SC and IM sites, but that the quantity of tissue developed is significantly greater in the IM implants.

At each of the sites, we observed the presence of numerous vessels within the collagenic matrix, homogeneously distributed in all the implants (FIG. 1C, D, black arrowheads). Their count revealed a significant difference between the IM and SC implants with a mean of 61.4±10.2 vessels/$mm^2$ and 51.10±10/$mm^2$ respectively (n=9; p=0.045). We also observed numerous multinucleated giant cells attached to the BCP particles (white arrowheads). These cells are identical to those which we identified as being osteoclasts in previous work (Trojani C. et al., Biomaterials, 27, 2006, 3256-3264). Their count revealed a mean of 88.51±14.60 osteoclasts/$mm^2$ in the IM implants and 93.13±14.40/$mm^2$ in the SC implants, a difference that is not statistically significant. The high resorption capacity of these cells is strongly suggested by the presence of microparticles and intercytoplasmic fragmentation crystals, by the irregularity of the contour of some BCP particles, their degradation texture with a lower and heterogeneous density. Finally, we observed the presence of cubic osteoblasts aligned at the surface of the BCP particles (FIG. 1C and insert, FIG. 5C, white arrows) and of numerous cells of the osteocyte type embedded in the collagen matrix (FIG. 1D, 2B, 3A, B black arrows). The mature osteoblast phenotype of these cells was demonstrated by the intracytoplasmic immunohistological detection of osteocalcin (FIG. 2A). Furthermore, all the implants were positive after Goldner's staining after 4 weeks of implantation, indicating that this neoformed tissue is mineralized (FIG. 2C).

Analysis of the 4-week IM implants by scanning electron microscopy made it possible to observe (FIG. 3) the microporosity of the BCP particles, the collagen matrix filling the interparticle spaces, the presence of functional capillaries containing erythrocytes (FIG. 3A, D, white arrow) and osteoclasts attached to the BCP granules (FIG. 3C, black arrows). Furthermore, it confirmed the presence of star-shaped cells of the osteocyte type possessing numerous extensions radiating in all directions, embedded in the collagen matrix and surrounded by a pericellular space of the osteoplast type (FIG. 3A insert, 3B).

The results obtained after 8 weeks of implantation did not reveal any significant difference with the 4-week implants. All the SC and IM implants are completely colonized by immature bone exhibiting the same histological characteristics.

3.2. Macroscopic and Microscopic Analysis of the SC and IM Implants of Coagulated Plasma/BCP In order to analyze the respective role of the plasma and the blood cells in the bone neoformation, we implanted in parallel for each mouse and at each site (SC and IM) an implant of coagulated blood/BCP and an implant of coagulated plasma/BCP.

The structure of the fibrin network of the two types of implant, coagulated blood/BCP and coagulated plasma/BCP, was analyzed by scanning electron microscopy. This showed that the fibrin mesh obtained with the coagulated blood was larger than that observed with the coagulated plasma (FIG. 4A, B). As expected, the red blood cells and the platelets are the predominant cells observed in the implants of coagulated blood/BCP. The preservation of their shape and their structure demonstrates good viability (FIG. 4A), which indicates that the mixture of blood and BCP particles has no deleterious effect on the blood cells.

Dissection and macroscopic examination of the implants of coagulated plasma/BCP after 4 and 8 weeks showed similar characteristics to those of the implants of coagulated blood/BCP, that is to say a firm consistency and numerous visible surface vessels (results not shown). Histological analysis after 4 weeks showed that the SC implants were all about 80% colonized (FIG. 5A) by neoformed bone. Analysis of the IM implants showed complete colonization in 75% of cases (FIG. 5B) and in 25% of cases, the presence of a small central zone of more fibrous and loose tissue (result not shown). At each of the sites, the neoformed fibrillar bone tissue exhibited the same characteristics as those of the tissue obtained in the implants of coagulated blood/BCP (FIG. 5C, 5D). In conclusion, these results demonstrate that the use of whole blood makes it possible to obtain complete colonization of the implants at both sites. The combination of coagulated plasma and BCP particles produces an incomplete colonization.

3.3 Macroscopic and Microscopic Analysis of Implants Composed of Coagulated Human Blood and 40-80 µm BCP Particles, after Subcutaneous Implantation in Immunosuppressed Mice We analyzed the bone formation induced by the biomaterial prepared from coagulated human blood around 40-80 µm BCP particles after implantation in nude-type immunosuppressed mice. In parallel, in the same animals, we implanted the biomaterial prepared from blood from C57BL/6 mice in order to compare, in the same recipient animal, the bone formation induced by mouse blood and that produced by human blood. After 6 weeks of implantation, the implants were collected, fixed and the histological analysis was carried out as previously described.

Even before the histological study, we observed the quite unusual hardness of the implants prepared from human blood while the implants of mouse blood had a more elastic consistency.

Histological analysis of the murine implants revealed an immature bone tissue of equivalent quality to that found during the previous experiments carried out in a syngenic system (implantation of C57BL/6 mouse blood in C57BL/6 mice). We observed a highly vascularized collagenic fibrillar tissue in which bone cells, osteoblasts, osteocytes and osteoclasts can be identified (FIG. 6A, 6B).

Histological analysis of the human implants gave very different results with colonization by a mature bone tissue. The bone cells are fewer, in favor of osteocytes. The supporting tissue exhibits an organization into better structured, aligned and more dense collagen fibers, having within it hematopoiesis plates characterized by the presence of immature hematopoietic cells such as erythroblasts and adipocytes (FIG. 6C, 6D). The hardness of these implants upon cutting suggested that this tissue was highly mineralized. We therefore obtained a mature lamellar bone tissue.

The difference in maturity of the bone tissues obtained after implantation of the human and murine bloods could result from different properties of the blood of these two species, properties linked to the cellular composition and/or to the protein composition, to growth factors, to soluble factors and to the fibrin network. Experiments will be carried out to try to understand the mechanisms involved.

Comparison of our results with those of the literature showed that the mature bone tissue which we obtained from human blood was very similar to the one described by several groups after implantation of human mesenchymal stromal cells (MSC) selected, amplified and differentiated ex vivo into osteoblasts and then combined with BCP powder and subcutaneously implanted into immunosuppressed mice.

All these results are therefore very promising for clinical application.

3.4 Influence of the Particle Size of BCP on Bone Formation

We tested 4 forms of BCP, three microparticle forms calibrated respectively between 40 and 80 µm, 80 and 200 µm and 200 and 500 µm, and a mixture of particles of 80-200 µm and of fine dust of much less than 40 µm in size, the proportion of fine dust being 40% by weight relative to the total weight of the mixture. Implants were prepared under the conditions already described, from C57BL/6 mouse blood and from each of these forms of BCP. Bone formation was analyzed after 8 weeks of subcutaneous implantation in syngenic C57BL/6 mice.

The results of FIG. 7 illustrate that the implants consisting of 80-200 µm microparticles very reproducibly produce the best colonization by an immature bone tissue having the characteristics already described (FIG. 7C, 7D). The presence of BCP dust (size of less than 40 µm) mixed with the 80-200 µm BCP microparticles is extremely deleterious for bone formation as shown in FIG. 7A. Indeed, colonization of the implants is observed which always remains strictly limited to the peripheral crown. The implants consisting of 40-80 µm grains produce good colonization but less reproducibly than the 80-200 µm implants. Indeed, inexplicably, a central colonization defect is sometimes observed as shown in FIG. 7B. Finally, the implants consisting of 200-500 µm grains are always colonized but by a more fibrous and loose tissue of a less satisfactory quality (FIG. 7E, 7F).

These results demonstrate that, in our biomaterial, the 80-200 µm granulosity is more favorable to bone formation at an ectopic site.

3.5 Determination of the Optimal BCP/Blood Ratio for Bone Reconstruction

It is possible to incorporate into our biomaterial variable quantities of BCP microparticles for the same volume of blood. The determination of the ideal ratio was an important step in its development. Several experiments for implantation at a subcutaneous site in mice, and preliminary experiments carried out at a bone site in Wistar rats and in Beagle dogs allowed us to specify the best BCP/blood ratios.

3.5.1. Implantation at a Subcutaneous Ectopic Site in Mice

We prepared implants consisting of a fixed quantity of blood (100 µl), a fixed quantity of $CaCl_2$ (10 µl) and an increasing quantity of 40-80 µm BCP microparticles: 10 mg, 30 mg, 50 mg and 70 mg, that is BCP/blood ratios of 10, 30, 50 and 70% weight/volume. The BCP particles were maintained in suspension in the blood during coagulation by rotating on a roller (method 1). These implants had equivalent sizes at the time of implantation, with respective volumes of: 112, 116, 120 and 124 µl.

As shown in FIG. 8, after 4 weeks of implantation, we observed that the final size of the implants was proportional to the initial weight of BCP incorporated, and that all the implants had an equivalent particle density. Moreover, the colonization by immature bone tissue was the same regardless of the BCP/blood ratio.

These results show that the homogeneous dispersion of the grains in the initial implant, obtained by rotation of the syringes during coagulation, is not maintained over time. On the contrary, a phenomenon of packing of the particles occurs which is probably linked to the natural degradation of the fibrin gel in vivo. As this packing results in the same concentration of grains for a given volume, regardless of the initial ratio, it seems logical that the osteoinduction phenomenon is the same.

The experiments subsequently carried out at a bone site confirmed these results.

3.5.2. Implantation at a Bone Site in Rats

We operate on a single femur per rat, the loss of substance is filled in with our biomaterial, autologous whole blood/BCP (80-200 µm). The rats are monitored clinically (absence of pain, deambulation, general condition) and radiologically by photographs at D0, D7, D15, D30, D45, D60 and D90. At the end of the third month, the animals are sacrificed, the femurs are collected and, after ablation of the osteosynthesis material, the bones are fixed in formalin before being embedded in methyl methacrylate resin and histological study.

During the first procedures, the implants were made to the size of the bone defect, with a proportion of particles of 50% weight/volume, that is 75 mg of BCP per 150 µl of whole blood collected from the animal pre-operatively. The coagulation is initiated by the addition of 15 µl of 2% $CaCl_2$ and the homogenization is produced by continuous rotation until coagulation is obtained so as to maintain the BCP particles in suspension in the blood and ensure the homogeneity of the biomaterial.

We observed very reproducibly and from the first x-ray photographs at D7, the appearance of a radiotransparent line between the bone surfaces and the implant (FIG. 9A), reflecting an absence of cohesion between the biomaterial and the diaphyseal sections. When the BCP is at maximum concentration in the blood, the microparticles sedimenting during the coagulation (method No. 2), a satisfactory cohesion between the biomaterial and the diaphyseal sections is observed (FIG. 9B).

3.5.3. Comparison of the Results Obtained with the Two Methods for Preparing the Implants In rats (FIG. 9B) and in dogs (FIGS. 10A and 10B) at a bone site, the x-ray analyses showed, with this new protocol, the absence of shrinkage of the implants on the x-rays of the front and the absence of a line on the x-rays of the side. In mice at an ectopic site, we did not observe differences in the results on bone formation.

3.5.4. Discussion

In the case of a bone implantation of a sedimented biomaterial (method 2), there is no reduction in the dimensions of the implant, as we can observe on the x-rays taken on rats and dogs, and if it was correctly fitted, in close contact with the bone, it benefits from the osteoconduction and osteoinduction phenomena in an optimum fashion.

The invention claimed is:

1. A method for manufacturing a biomaterial, the method comprising:
   (i) mixing a biphasic calcium phosphate (BCP) comprising hydroxyapatite (HA) and β-tricalcium phosphate (β-TCP) in an HA/β-TCP weight/weight ratio of between 5/95 and 95/5, in the form of granules whose size is between 40 and 500 μm, with blood or with a bone marrow aspirate, in a proportion ranging from 10 to 90 g by weight of BCP per 100 mL of blood or bone marrow aspirate to give a mixture;
   (ii) adding to the mixture of (i) at least one coagulating agent in a sufficient quantity to cause coagulation of blood or of the bone marrow aspirate, wherein the concentration of the coagulating agent is from 1 mM to 50 mM; and
   (iii) mixing under conditions promoting homogenization of the BCP while the coagulation occurs, and wherein the biomaterial is in the form of a malleable homogeneous paste.

2. The method of claim 1, wherein the at least one coagulating agent comprises calcium and is a biocompatible calcium salt.

3. The method of claim 1, wherein the blood is employed and is collected beforehand from a donor compatible with a recipient for whom the biomaterial is intended.

4. The method of claim 1, wherein the blood is employed and is collected beforehand from a recipient for whom the biomaterial is intended.

5. The method of claim 1, wherein the mixture comprises the BCP, the blood, and the coagulating agent, is allowed to stand during the coagulation so as to allow the BCP to sediment and to form an implant saturated with BCP.

6. The method of claim 1, wherein (i) to (iii) are carried out in an inner cavity of a syringe or in a tube closed at its ends.

7. The method of claim 1, which comprises mixing from 50 to 90 g by weight of BCP, per 100 mL of blood or bone marrow aspirate.

8. A biomaterial comprising a BCP in the form of granules having a size of between 40 and 500 μm dispersed substantially homogeneously in a three-dimensional network of blood proteins or in a network of bone marrow proteins obtained by a method consisting essentially of:
   mixing a biphasic calcium phosphate (BCP) comprising hydroxyapatite (HA) and β-tricalcium phosphate (β-TCP) in an HA/β-TCP weight/weight ratio of between 5/95 and 95/5, in the form of granules whose size is between 40 and 500 μm, with blood or with a bone marrow aspirate, and with at least one coagulating agent, in a sufficient quantity to cause coagulation of the blood or of the marrow aspirate, and
   allowing the mixture comprising the BCP, the blood or bone marrow aspirate and the coagulating agent to coagulate,
   wherein, in the mixture:
   BCP is present in a proportion ranging from 10 to 90 g by weight of BCP, per 100 mL of blood or bone marrow aspirate, and
   the concentration of the coagulating agent is from 1 mM to 50 mM, and wherein the biomaterial is in the form of a malleable homogeneous paste.

9. The biomaterial of claim 8, wherein the BCP granules have a size ranging from 80 to 200 μm.

10. The biomaterial of claim 8 further comprising at least one additive selected from the group consisting of: a polymer, a ceramic particle, a pharmaceutical molecule, a growth factor, a natural biomarker or a synthetic biomarker, a contrast agent, a tissue preparation and a cell preparation.

11. A method for filling in a bone defect, the method comprising implanting the biomaterial of claim 8 into a bone.

12. A method of producing bone tissue, the method comprising growing the bone tissue upon a support comprising the biomaterial of claim 8 in vitro or ex vivo.

13. A method of producing a bone implant, the method comprising combining the biomaterial of claim 8 in vitro or ex vivo with a bone tissue or prosthesis.

14. The biomaterial of claim 8, wherein the BCP comprises hydroxyapatite (HA) and β-tricalcium phosphate (β-TCP) in an HA/β-TCP weight/weight ratio of between 30/70 and 80/20.

15. The biomaterial of claim 14, wherein the BCP comprises hydroxyapatite (HA) and β-tricalcium phosphate (β-TCP) in an HA/β-TCP weight/weight ratio of between 40/60 and 60/40.

16. The biomaterial of claim 8, wherein the BCP is porous and the pores have sizes from 50 nm to 150 μm.

17. The biomaterial of claim 8, wherein the BCP is porous and the pores have sizes from 1 μm to 50 μm.

18. The biomaterial of claim 8, wherein the at least one coagulating agent comprises calcium and is a biocompatible calcium salt.

19. The biomaterial of claim 8, wherein blood is employed and is collected beforehand from a donor compatible with a recipient for whom the biomaterial is intended.

20. The biomaterial of claim 8, wherein blood is employed and is collected beforehand from a recipient for whom the biomaterial is intended.

21. The biomaterial of claim 8, wherein the mixture comprising the BCP, the blood and the coagulating agent, is allowed to stand during the coagulation so as to allow the BCP to sediment.

22. The biomaterial of claim 8, wherein BCP is in a proportion ranging from 30 to 90 g by weight of BCP per 100 mL of blood or bone marrow aspirate.

23. The biomaterial of claim 8, further comprising the step of mixing under conditions promoting homogenization of the BCP while the coagulation occurs.

24. The biomaterial of claim 22, BCP is in a proportion ranging from 50 to 70 g by weight of BCP, per 100 mL of blood or bone marrow aspirate.

25. The biomaterial of claim 8, wherein the concentration of the coagulating agent in the mixture is from 3 to 35 mM.

* * * * *